United States Patent [19]

Grube et al.

[11] Patent Number: 4,743,242

[45] Date of Patent: * May 10, 1988

[54] DISPOSABLE DIAPER WITH REFASTENABLE TAPE SYSTEM

[75] Inventors: Herbert E. Grube; Michael A. Sciaraffa, both of Outagamie County; Mark L. Kaspar; Leonard M. Kaczmarzyk, both of Winnebago County, all of Wis.

[73] Assignee: Kimberly-Clark Corporation, Neenah, Wis.

[*] Notice: The portion of the term of this patent subsequent to Apr. 7, 2004 has been disclaimed.

[21] Appl. No.: 7,057

[22] Filed: Mar. 17, 1987

Related U.S. Application Data

[63] Continuation of Ser. No. 637,929, Aug. 6, 1984, Pat. No. 4,655,761.

[51] Int. Cl.$^4$ .............................................. A61F 13/16
[52] U.S. Cl. .................................................. 604/389
[58] Field of Search .................... 604/389, 390, 385.1, 604/387, 378; 428/500

[56] References Cited

U.S. PATENT DOCUMENTS

| | | | |
|---|---|---|---|
| 3,484,835 | 12/1969 | Trounstine et al. | 428/500 |
| 3,616,114 | 10/1971 | Hamaguchi | 428/41 |
| 3,630,201 | 12/1971 | Endcres | 604/390 |
| 3,853,129 | 12/1974 | Kozak | 604/390 |
| 3,948,267 | 4/1976 | Karami | 604/390 |
| 3,951,149 | 4/1976 | Ness et al. | 604/390 |
| 3,967,624 | 7/1976 | Milnamow | 604/390 |
| 4,049,001 | 9/1977 | Tritsch | 604/390 |
| 4,067,337 | 1/1978 | Ness | 604/390 |
| 4,100,921 | 7/1978 | Schaar | 604/390 |
| 4,237,889 | 12/1980 | Gobran | 604/389 |
| 4,399,249 | 8/1983 | Bildusas | 604/389 X |
| 4,655,761 | 4/1987 | Grube et al. | 604/389 |

FOREIGN PATENT DOCUMENTS

| | | |
|---|---|---|
| 1579799 | 9/1981 | United Kingdom . |
| 2108370 | 5/1983 | United Kingdom . |
| 2114449 | 8/1983 | United Kingdom . |

*Primary Examiner*—John D. Yasko
*Attorney, Agent, or Firm*—Paul A. Leipold; Donald L. Traut; Jeremiah J. Duggan

[57] ABSTRACT

The invention relates to a system for fastening refastenable garment such as diaper or incontinent garment in which a tape and polymer backing material for the garment are provided such that tape may be removed after refastening to the diaper without tearing of the polymer material. The system of the invention utilizes a polypropylene tape material that is embossed on the outer surface and smooth on the adhesive-carrying surface. The adhesive on the tape is a semihard adhesive that provides high adhesion values to the polymer that nevertheless may be peeled free for removal of the tape and subsequent refastening. The polymer forming the outer backing if the diaper is a relatively thick, embossed polymer sheet. In the refastenable system of the invention the strength and adherence of the tape to the strong, embossed polymer backing sheet is controlled so as to achieve secure fastening with release of the adhesive from the embossed sheet without tearing.

8 Claims, 2 Drawing Sheets

DISPOSABLE DIAPER WITH REFASTENABLE TAPE SYSTEM

This is a continuation of co-pending application Ser. No. 637,929, filed Aug. 6, 1984, now U.S. Pat. No. 4,655,761.

TECHNICAL FIELD

This invention relates to disposable diapers having a pressure-sensitive adhesive closure. More particularly, the invention relates to disposable diapers having a reopenable and resealable pressure-sensitive adhesive closure.

BACKGROUND ART

It has become very common to use adhesive tape tabs on disposable diapers. However, as there is often a need for reuse of a disposable diaper that has not been soiled, there has been a need for a refastenable tape system. The conventional tape system would tear the poly backing material of a diaper when removed from the front. Therefore, they could only be refastened by use of additional tape that was awkward and inconvenient to the user.

There have been proposed and commercialized refastenable tape systems in which a piece of tape is transferred to the front of a diaper and serves as a target area for refastening of the diaper. Such a system is disclosed in U.S. Pat. No. 3,951,149, Ness et al. and in U.K. Pat. No. 2,091,986 assigned to Unicharm. However, such tape systems while providing reliable refastenability have disadvantages. These disadvantages include the possibility for the consumer to misuse the tape structure such that the piece of tape to be transferred to the front is thrown away. Further, it is possible that the adherence of the main tape for the refastenable holding tape will be so great that the tape will be torn from the front of the diaper. Other disadvantages are that the target tape (transferred to the diaper front) may become contaminated with a material such as the creams used in treating diaper rash or the person fastening the diaper may miss the target tape when refastening the diaper.

U.K. publication No. GB 2,114,449 to Korpman discloses a disposable diaper provided with a pressure-sensitive adhesive that permits reopening of the diaper numerous times without substantial damage to the polyethylene backing sheet or the adhesive closure. This system is believed to have the disadvantage that the U.K. British Pat. No. 1,597,799 assigned to Johnson & Johnson also discloses a single-tape refastenable diaper. In the 799 patent the diaper is claimed to have a tape that has a "quick stick" of about 7 oz. per inch, and peel adhesion of substantially no more than 8.3 oz. per inch. This system is believed to provide an inadequate fastening adhesion and, therefore, would be unreliable in that some diapers will come open during use.

U.S. Pat. No. 4,399,249 to Bildusas discloses adhesive suitable for forming contact bonds that are resealable to polyethylene surfaces at room temperature. The adhesive composition disclosed therein is set forth as suitable for releasable and resealable sealing strips for storage or sandwich bag products.

U.S. Pat. No. 4,376,147 to Byrne et al. discloses a plastic film having a matte finish. The film was disclosed as particularly suitable for use with disposable diapers.

DISCLOSURE OF THE INVENTION

It is an object of this invention is overcome disadvantages of prior diaper fastening systems.

It is a further object of this invention to provide a single tape refastenable diaper that securely fastens a diaper.

It is another object of this invention to provide a diaper backing polymer film that in combination with a selected tape and adhesive provides a reliable refastenable single-tape closing system that will not open accidentally when worn.

It is an object of this invention to provide a single refastenable tape system suitable for multiple opening and closing.

The invention relates to a system for fastening refastenable garments such as diapers or incontinent garments in which a tape and polymer backing material for the garment are provided such that tape may be removed after refastening to the garment without tearing of the polymer material. The system of the invention utilizes a polypropylene tape material that is embossed on the outer surface and smooth on the adhesive-carrying surface. The adhesive on the tape is a semihard adhesive that provides high adhesion values to the polymer that nevertheless may be peeled free for removal of the tape and subsequent refastening. The polymer forming the outer backing of the diaper is a relatively thick embossed polymeric sheet. In the refastenable system of the invention the strength and adherence of the tape to the strong embossed polymer backing sheet is controlled so as to achieve secure fastening with release of the adhesive from the embossed sheet without tearing.

MODES FOR CARRYING OUT THE INVENTION

The system of the invention has many advantages over prior systems. It allows refastenability without the need to refasten on the same site as was fastened the first time. It has advantages over other refastenable single-tape systems in that the fastening to the front of the diaper is more secure but still may be released on pulling the tape free without tearing the polymer backing of the diaper. These and other advantages of the invention will become apparent from the description below.

Figure 1:
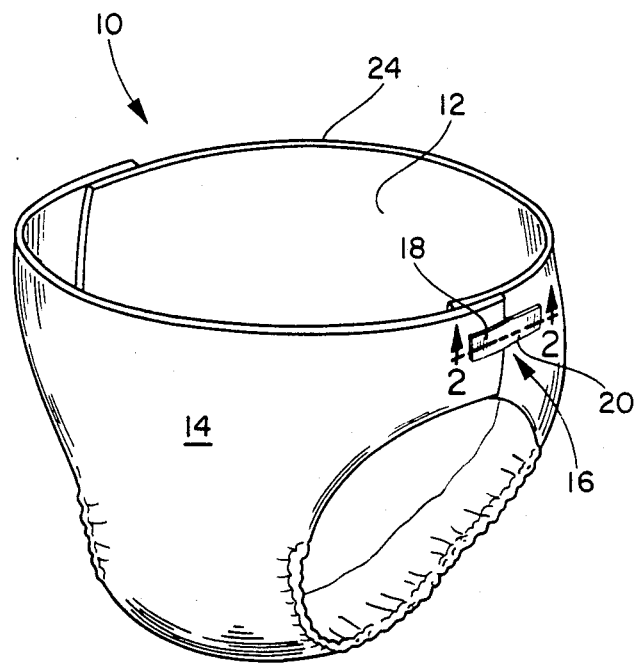
FIG. 1 is a view of a diaper illustrating use of the sealing system of the invention.

The invention is directed to the refastenable tape structure for use on a disposable garment such as the diaper as illustrated in FIG. 1. In FIG. 1 there is illustrated a diaper 10 that is composed of a front portion 12 and a rear portion 14. The diaper 10 carries a tape 16. The tape has a permanently fastened first tape portion 18 adhered to the diaper back 14. There is a removable and refastenable second portion 20 that may be placed on the front of the diaper 12. The diaper of incontinent garment may be of any structure, including a diaper with elastic legs such as illustrated by diaper 10. Further, the diaper could, if desired, have elastic at waist 24.

Figure 2:
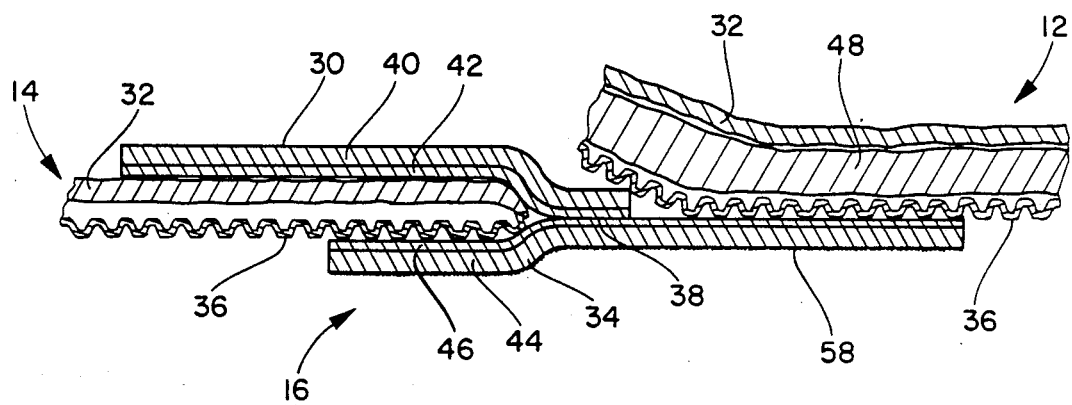
FIG. 2 is a cross-section along lines 2—2 of FIG. 1.

In FIG. 2 there is an illustration of a diaper tape and fastening system in accordance with the invention. The fastening system 16 is of the conventional "Y" tape structure in which the diaper back portion 14 has a tape 30 on the inner portion that is adhered to the pervious lining material 32, and another tape 34 that is adhered to the backing material 36 as well as to the tape 30 in area 38. Tape 30 is composed of a polymer or paper layer 40 that has applied to it an adhesive 42. Tape 34 is composed of a layer of polymer material 44, preferably polypropylene, and an adhesive layer 46. The tape 34 is adhered to the front of the diaper 12 onto the garment backing material 36. The diaper front 12 has an absorbent layer 48 between the impermeable backing 36 and the pervious liner material 32. It is noted that the drawings of FIG. 2 are not in scale in that the surface of the polymer sheet 36 has been exaggerated in thickness compared to the thickness of the absorbent structure 48. The description below will when necessary specify parameters and thicknesses and the drawing is only illustrative and not to scale. Further, the diaper absorbent material and pervious inner liner do not form a part of this invention.

Figure 3:
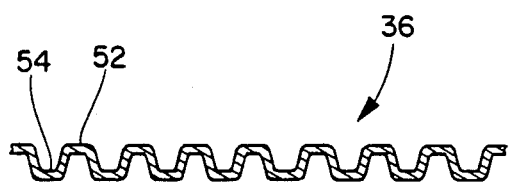
FIG. 3 is a cross-sectional view of a portion of polymer backing sheet in accordance with the invention.

Illustrated in FIG. 3 is a section of the polymer backing material 36. This backing material has an embossed pattern of lands 52 and valleys 54. The polymer, therefore, has a greater caliber thickness than it does nominal thickness of the polymer sheet. The tape backing material 54 has an embossed surface 58.

The tape layer of polymer material 44 forming a part of the invention has an embossed surface that has a fine matte embossing. The embossed finish may be formed by application of an embossed roll to preformed tape. Alternatively, an embossed surface may be formed by casting and forming the tape on a surface having an embossed surface. The matte surface is thought to improve performance by aiding the gripping of the surface and making the tape less likely to tear. The tape has a surface roughness within the Gurley range of 200 seconds to 50,000 seconds (TAPPI T-479). The preferred roughness of about 200 seconds to about 20,000 seconds (TAPPI T-479) which is preferred because gripability. Lower Gurley numbers mean a rougher surface and better gripability of the tape.

The preferred composition of the polymer layer of the tape material is a polypropylene film that has a tensile strength of greater than 9 pounds per inch. It is preferred that a polypropylene film having a tensile yield of 12 pounds per inch (Tested by PSTC 31) be utilized as this tape gives good release properties and strength. The elongation of the preferred polypropylene tape is about 600 percent minimum at break (tested by PSTC 31).

The stiffness of the tape is generally between about 30 and 100 Gurley units. It is preferred that the tape has about 60 Gurley units stiffness as this will cause reduced irritation if the tape is exposed to the skin of the wearer. The Gurley stiffness tester is a standard unit of the Testing Machine Company. The tape thickness will affect its stiffness and abrasion of the wearer. It is generally preferred that the embossed polypropylene tape caliper thickness of between about 3.5 and about 5.0 mils, for the best combination of strength, flexibility, and nonabrasion. The unembossed thickness is not believed to be greatly different from the caliper thickness as the embossing is slight; probably unembossed thickness is no more than 0.5 mil less than embossed film thickness. It is theorized that the flexible, thin tape and thick, strong backing material for the diaper combine to form the refastenable tape of the invention that securely fastens but also can be reliably released and refastened.

In contrast to the outer surface of the tape, the adhesive side of the tape rather than having a rough, matte gripping surface, has a smooth surface. This is somewhat surprising in that the traditional paper tapes were thought to be smooth and the improvement in the tape resulting from better polymer surface was unexpected. The smooth surface bearing the adhesive apparently allows a better compromise between the security and the refastenability, thereby allowing the tape to achieve good adherence to the polymer backing of the diaper but at the same time be refastenable. The term "smooth" as used herein in describing the adhesive side of the tape may be described as wetting about 99% of a smooth, glossy Plexiglas surface whereas the previous paper tape only wet about 70% of a smooth, clear Plexiglas when the tape is viewed from the opposite side of the Plexiglas to which it is adhered.

This tape system may use any suitable adhesive that gives the desired quick-stick and static shear properties. The composition of the tape adhesive is not considered critical, and it may be selected from one of the well-known adhesives such as styrene isoprene block copolymer based adhesives. The quick-stick properties of the adhesive generally are between about 350 and 950 grams per inch. The performance attributes found to be preferred are a quick-stick to the diaper polyethylene of between about 550 grams per inch and about 750 grams per inch of good refastenability. The optimum amount of quick-stick is about 650 grams per inch for secure fastening of the diaper. The quick-stick test is performed by placing a one-inch width of the tape onto a stainless steel carrier and removing the tape at a 90 degree angle. This test is modified from PSTC No. 5 by using polyethylene substrate and 17.1 gm/cm$^2$ pressure.

The static shear property of the tape also should be controlled for the system of the invention. The preferred static shear is greater than 100 minutes, for a 500 gram weight, for one-quarter square inch area adhered. The test is variation of PSTC No. 7, performed at 100 degrees F. in which a quarter-inch square portion of the tape is adhered to a steel bar, the quarter-inch square portion is the last half inch of a length of a half-inch tape. To the remaining portion of the tape is adhered at 500 gram weight. The preferred static shear is about 250 minutes to give reliable and secure fastening of the diaper. The static shear of greater than 250 minutes unexpectedly has the effect of reducing buildups on equipment that is used in forming the tapes onto the diaper. The preferred static shear is important is resisting buildup of adhesive and cut tape particles on the cutter devices in the forming area. The adhesives having the specified properties of static shear and quick-stick are those that are firm and do not allow their being pressed to a significant extent into the embossed portion of the backing sheet. If they are not pressed into the valleys of the embossed portion, the tapes are more likely to release without tearing of the sheet. The viscoelasticity is such that they have a resistance to such flow at temperatures that a diaper is used.

A diaper tape of the invention has the property of peeling from the polymer backing sheet of the diaper without tearing. The ability to peel from the diaper is measured by the 180 degree peel test. In this test a piece of tape is adhered to a piece of the 1.5 mil preferred diaper polymer backing sheet that is carried on a steel panel. The one-inch wide tape is pressed onto the poly with a force of 4½ lb. rubber roller. It is then removed by peeling at a 180 degree angle at separation speeds of 300 mm/min and 1000 mm/min. Unexpectedly, it was found that the tape adhesion system of this invention has relatively high peel adhesion at a 300 mm/min separation rate and relatively low peel adhesion at a 1000 mm/min. Average peel forces between about 400 grams per inch and about 575 grams per inch at 300 mm/min are preferred for secure fastening. Average peel forces, between 200 gms/inch and 400 grams per inch, at 1000 mm/min separation rate are preferred in order to unfasten and refasten without irreversably stretching or tearing of the diaper polyethylene. It is theorized that the low peel force at the fast peel rate of 1000 mm/min is important as the fast peel more closely resembles the peeling of the diaper tape by the mother in using the diaper.

The property of the fastened aged tape also is pertinent to the invention. The tape after three hours at 100 degrees F. preferably has between about 70 and 100 percent of the initial peel strength. The upper limits preferably are about 105 percent of the initial force. The dwell time properties of the aging are important as they stimulate use conditions.

The polymer garment backing material of the invention is selected so as to give a surface that will aid in the adherence, release and refastenability of the tape system. The wetting tension of the polymer surface is a property that is indicative of a surface that has the desired properties. Typical suitable wetting tensions are between about 34 and 38 dynes per square centimeter. It is preferred that the polymer sheet has a wetting of a up to about 34 dynes per square centimeter on the outer surface as the material is not receptive to adhesive to a large degree and operates well with the aggressive tape adhesives. The wetting tension is measured by the ASTM D2578 test. The polymer may be treated by corona treatment to give the desired surface tension. The type of embossed surface also affects the wetting tension. When a less aggressive adhesive is used, then a higher wetting tension is suitable.

Figure 4:
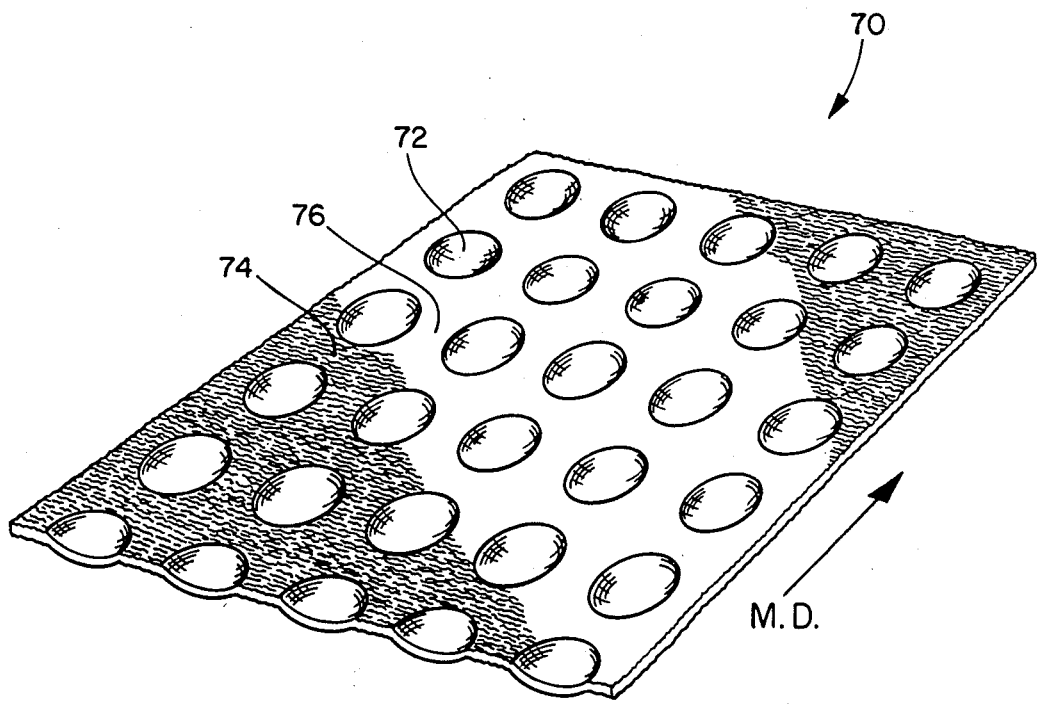
FIG. 4 is a perspective view of a sheet of 1 suitable for the diaper backing materials.
Figure 5:
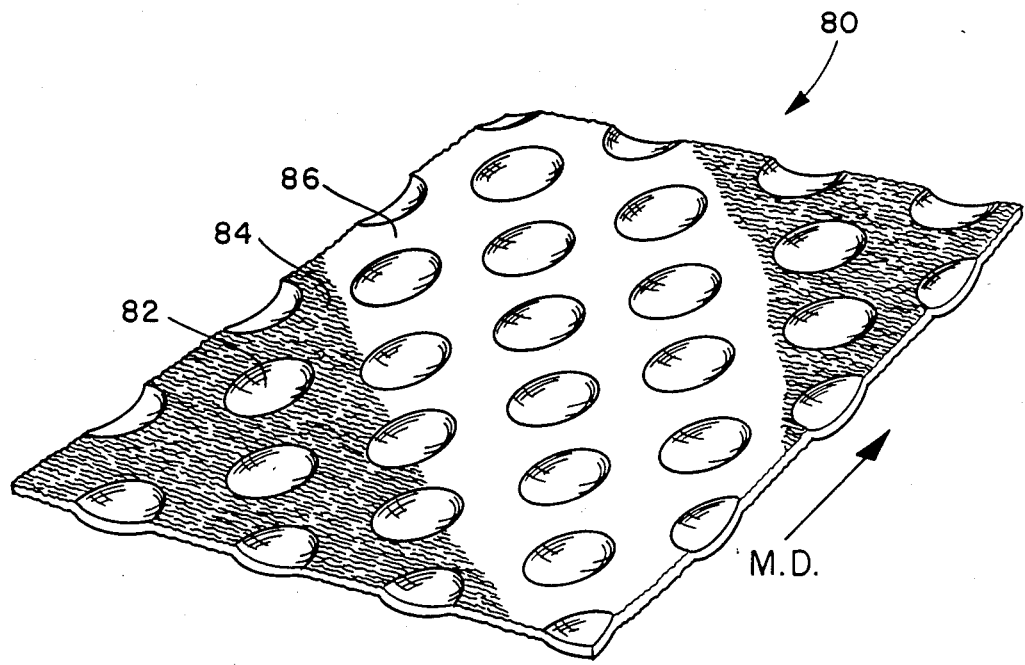
FIG. 5 is a perspective view of an alternate backing film for the diaper fastening system of the invention.

The garment backing film of this invention is preferably embossed so as to provide a surface that will be gripped by the tape but allow the tape to be unfastened from the polymer without tearing. As illustrated in FIG. 4, the film 70 has an embossed finish that from the outside surface where fastening tape is placed may be viewed as a series of ridges running parallel to the direction of the polymer and perpendicular to the edge direction of the polymer. It is noted that the drawing indicates the machine direction (MD) with the ridges 74 running perpendicular to the machine direction and ridges 76 running parallel with the machine direction. The interstices between the ridges form valleys 72. In FIG. 5 is illustrated an alternate embossed surface for the film of the invention. Sheet 80 of FIG. 5 also is illustrated with the outside facing (tape-contacting) surface upward. It, again, is formed with a series of ridges 84 and 86 intersecting at right angles. Spaces between the ridges form interstices or valleys 82. The lines forming the ridges are located about 45 degrees from the machine direction (MD) of the polymer.

The embossed pattern for the garment backing sheet of the invention may be any embossed pattern that provides good refastenability. A suitable embossed pattern has been found to be between about 130 and about 200 lines per inch in each direction to form a polymer sheet suitable for the backing material. It has been found that a preferred number of lines per inch is between about 145 and about 185 for good refastenability and pleasing matte finish. An optimum number of lines has been found to be about 165 lines in each direction for best refastenability characteristics and pleasing surface.

The amount of the polymer garment backing sheet surface exposed to the adhesive of the diaper tape will vary depending on the area of the ridges on the embossed film. Generally these ridges are formed so as to be flat. A suitable amount of the surface area of the sheet occupied by the ridges on the outside tape-contacting surface would be between about 50 percent and 70 percent when viewed on a one hundred times enlarged gold-surfaced piece of film. An optimum amount of ridge area has been found to be about 60 percent of the total sheet area for best refastenability and pleasing surface texture for the preferred backing sheets of the invention. The relationship of the ridges with the machine direction of the sheet does not appear to be critical. Further, it is believed that the ridge lines do not necessarily need to be perpendicular to each other as long as the specified amount of surface area is exposed to the diaper tape adhesive. It is noted that the drawings of FIGS. 4 and 5 illustrate the valleys 72 and 82 as rounded even though the lines of the ridges are embossed as lines. This effect is apparently caused by deformation of the film during embossing that results in rounded rather than square valleys.

The polymer garment backing sheet of the invention may have any suitable polymer thickness. It is been found that the suitable sheet thickness is between about 1.2 and about 1.7 mils. It is preferred that the sheet be between about 1.3 and 1.5 mils thickness for refastenability without tearing of the polymer. Gauge thickness is the thickness of smooth sheet that would be formed if the polymer of the sheet was used to form a smooth non-embossed film. The embossed pattern gives the sheet a caliper thickness of between about 2.0 mils and about 3.0 mils. It is preferred that the caliper thickness be about 2.3 mils to about 2.7 mils for good refastenability. The embossed finish gives the film a matte appearance.

The polymer composition of the garment backing film of the invention may be any suitable composition. It is preferred that the film be a low density blend of linear low density and high density polyethylene. The blend of high and low density and/or linear low density polyethylene has been found to give greater cross direction tensile strength, thereby allowing a strong, thin film.

The film tensile strength in the cross-machine direction may be between about 700 and about 1100 grams and preferably is in the range of between 800 and 950 grams per inch at about 25 percent elongation. Yield point preferably is about 950 to about 1100 grams per inch to the point where the film exceeds its elastic limit which usually occurs at about 50 to 75 percent elongation.

Therefore, it can be seen from the above description that by controlling the properties of the tape, adhesive, and polymer backing sheet, the refastenable tape may be formed that has a high peel strength, giving secure fastening of the diaper while at the same time allowing the tape to be removed and refastened without tearing of the polymer. This is in contrast to other systems that in order to prevent tearing of polymer have utilized less aggressive adhesives, thereby creating problems of the tape not adhering to the surface of the polymer when it was fastened. The combination of thick flexible tape, a relatively thick backing material and an aggressive adhesive act together to give a securely fastenable tape that is also refastenable.

In view of the above detailed description of the invention, it will be apparent to a person of ordinary skill in this art that variations of the fastening system of this invention may be employed, and the desired results may still be achieved. Further, while the invention is described with relation to the testing of diapers, the tape fastening system of the invention also is suitable for use with incontinent garments or disposable gowns. Further, the refastenable tape system of the invention may find use in plastic bags or other articles requiring refastenability.

We claim:

1. A refastenable garment comprising moisture-impermeable embossed backing sheet and a refastenable pressure-sensitive adhesive fastening tape wherein:
   (1) said fastening tape comprises:
     a polypropylene polymer having a matte finished outer surface,
     a smooth inner adhesive-coated surface,
   (2) said embossed backing sheet comprises:
     a film thickness of about 1.2 to about 1.7 gauge,
   (3) said tape and said backing have:
     a 180 degrees peel of between about 400 and about 575 grams per inch at a 300 mm/min peel speed.

2. The garment of claim 1 wherein said tape comprises polypropylene film with a tensile yield of about 12 pounds per inch.

3. The garment of claim 1 wherein said tape comprises a polypropylene film with an elongation of about 600 percent minimum at break.

4. The garment of claim 1 wherein said tape has a stiffness of between about 30 and about 100 Gurley units.

5. The garment of claim 1 wherein said tape has a quick-stick between about 350 and about 950 grams per inch to said backing sheet.

6. The garment of claim 1 wherein said tape has a quick-stick between about 550 and about 750 grams per inch to said backing sheet.

7. The garment of claim 1 wherein said 180 degrees peel is between about 80 and about 100 percent of the initial 180 degrees peel after 3 hours at 100° F.

8. The garment of claim 1 wherein said polypropylene fastening tape has a tensile yield of greater than about 9 pounds per inch.

* * * * *